United States Patent
Salamone et al.

(10) Patent No.: US 7,641,893 B2
(45) Date of Patent: Jan. 5, 2010

(54) CONFORMABLE SOLVENT-BASED BANDAGE AND COATING MATERIAL

(75) Inventors: Ann Beal Salamone, Boca Raton, FL (US); Joseph C. Salamone, Boca Raton, FL (US)

(73) Assignee: Rochal Industries, LLP, Boca Raton, FL (US)

( * ) Notice: Subject to any disclaimer, the term of this patent is extended or adjusted under 35 U.S.C. 154(b) by 0 days.

(21) Appl. No.: 11/465,237

(22) Filed: Aug. 17, 2006

(65) Prior Publication Data

US 2007/0041935 A1 Feb. 22, 2007

Related U.S. Application Data

(60) Provisional application No. 60/708,858, filed on Aug. 17, 2005, provisional application No. 60/708,898, filed on Aug. 17, 2005.

(51) Int. Cl.
*A61K 31/765* (2006.01)

(52) U.S. Cl. .................... 424/78.31; 424/78.03

(58) Field of Classification Search .............. 424/78.31, 424/447, 78.02, 78.06; 602/52; 156/329
See application file for complete search history.

(56) References Cited

U.S. PATENT DOCUMENTS

| | | | |
|---|---|---|---|
| 3,667,472 A * | 6/1972 | Halpern | ................ 606/214 |
| 3,940,362 A | 2/1976 | Overhults | |
| 4,313,865 A | 2/1982 | Teramoto et al. | |
| 4,560,723 A | 12/1985 | Millet et al. | |
| 4,987,893 A | 1/1991 | Salamone et al. | |
| 5,103,812 A | 4/1992 | Salamone et al. | |
| 5,140,084 A | 8/1992 | Mikuni et al. | |
| 5,214,093 A | 5/1993 | Nell et al. | |
| 5,259,835 A | 11/1993 | Clark et al. | |
| 5,328,687 A | 7/1994 | Leung et al. | |
| 5,928,611 A | 7/1999 | Leung | |
| 5,981,621 A | 11/1999 | Clark et al. | |
| 6,010,714 A | 1/2000 | Leung et al. | |
| 6,143,352 A | 11/2000 | Clark et al. | |
| 6,143,805 A | 11/2000 | Hickey et al. | |
| 6,183,593 B1 | 2/2001 | Narang et al. | |
| 6,217,603 B1 | 4/2001 | Clark et al. | |
| 6,358,503 B1 | 3/2002 | Gerrish | |
| 6,383,502 B1 | 5/2002 | Dunshee et al. | |
| 6,455,064 B1 | 9/2002 | Narang et al. | |
| 6,479,725 B1 | 11/2002 | Brothers | |
| 6,565,840 B1 | 5/2003 | Clark et al. | |
| 6,607,631 B1 | 8/2003 | Badejo et al. | |
| 6,607,632 B1 * | 8/2003 | McDonnell et al. | ...... 156/331.2 |
| 6,746,667 B2 | 6/2004 | Badejo et al. | |
| 2004/0223946 A1 | 11/2004 | Kidd et al. | |
| 2006/0030808 A1 * | 2/2006 | Kennedy | .................... 602/41 |

OTHER PUBLICATIONS http://www.sigmaaldrich.com/catalog/ProductDetai.*
http://www.osha.gov/dts/chemicalsampling/data/CH_231525.html.*
http://en.wikipedia.org/wiki/Polydimethylsiloxane.*
U.S. Appl. No. 09/430,289, filed Oct. 29, 1999, D'Alessio, et al.
Davis, et al.,"An Octyl-2-Cyanoacrylate Formulation Speeds Healing of Partial-Thickness Wounds", Dermatol Surg, 27(9):783-88 (2001).
Eaglstein, et al., "A Liquid Adhesive Bandage for the Treatment of Minor Cuts and Abrasions", Dermatol Surg, 28(3): 263-67 (2002).
Singer, et al., "Comparative trial of octyl-cyanoacrylate and silver sulfadiazine for the treatment of full-thickness . . . ", Wound Repair and Regeneration, 7: 356-361 (1999).
Singer, et al., "Evlauation of a new liquid occlusive dressing for excisional wounds", Wound Repair and Regeneration, 11: 181-87 (2003).
Vauthier, et al., "Poly(alkylcyanoacrylates) as biodegradable materials for biomedical applications", Advanced Drug Delivery Reviews, 55:519-548 (2003).

* cited by examiner

*Primary Examiner*—Michael G. Hartley
*Assistant Examiner*—James W. Rogers
(74) *Attorney, Agent, or Firm*—Novak Druce+Quigg; J. Rodman Steele, Jr.; Gregory M. Lefkowitz

(57) ABSTRACT

Liquid hemostatic coating materials comprise a cyanoacrylate monomer and a solvent system comprising a volatile, non-reactive liquid that is non-stinging and non-irritating to a user. The material forms a coating or bandage in the form of a film that when applied and adhered to a surface or to the skin of a user inhibits the application surface from adhering to another surface.

18 Claims, No Drawings

CONFORMABLE SOLVENT-BASED BANDAGE AND COATING MATERIAL

CROSS-REFERENCE TO RELATED APPLICATIONS

This application claims the priority of U.S. Provisional Application No. 60/708,858, filed Aug. 17, 2005, and U.S. Provisional Application No. 60/708,898, filed Aug. 17, 2005, both entitled CONFORMABLE SOLVENT-BASED BANDAGE AND COATING MATERIAL, which are incorporated herein by reference in their entirety.

FIELD OF INVENTION

This invention relates generally to hemostatic coating materials that are useful for protecting and repairing surfaces such as biological surfaces, including surgical sites, skin and mucous membranes. The hemostatic liquid adhesive materials are comprised of a polymerizable cyanoacrylate monomer component and a non-stinging, non-irritating, non-reactive, volatile liquid, wherein the generated coating does not adhere to a second surface. The hemostatic liquid adhesive materials may also comprise a silane-containing polymer component, and preferably a siloxysilane polymer, to provide enhanced forming.

BACKGROUND OF THE INVENTION

Cyanoacrylates have found use as liquid adhesive bandages, particularly butyl and octyl cyanoacrylates (U.S. Pat. Nos. 6,183,593; 6,143,805). These materials provide hemostasis with quick film formation and they are especially useful for closing thin wounds, such as those created by paper or razor cuts. Wounds that are in high flex areas are not suitable for treatment with cyanoacrylates as they tend to increase scarring, if well adhered, or to delaminate quickly, if not well adhered, due to their intrinsic brittleness. Polydimethylsiloxanes have been blended with cyanoacrylates to increase flexibility and elasticity (U.S. Pat. Nos. 6,746,667, 6,183,593, 5,140,084). Cyanoacrylates have low moisture vapor transmission rates and, hence, do not allow water vapor to equilibrate at the wound site to allow for optimum wound healing. Cyanoacrylates are also known for their ability to adhere two surfaces together quickly, which is a benefit for many surgical and repair applications but is problematic for use as a hemostatic agent or a liquid adhesive bandage where the user does not desire to adhere two biological surfaces or to another object, e.g. finger to finger or foot to floor.

Additionally, cyanoacrylate monomers when used as liquid adhesive bandages have been found to cause patient discomfort when applied to the skin as polymerization rapidly occurs when placed on a wet surface, generating heat. In addressing this problem, U.S. Pat. No. 6,010,714 discloses a biocompatible monomer (preferably a cyanoacrylate) with an effective amount of a heat dissipating liquid or solid to reduce the exothermic polymerization temperature of the cyanoacrylate. For the heat dissipating liquids cited, which include ethers, ketones, chlorofluorocarbons, alkanes, alcohols, alkenes and mixtures thereof, each of these organic solvents would cause stinging or irritation on an open wound, thus compromising their use in providing patient comfort and enhanced health. Additionally, U.S. Pat. No. 6,010,714 discloses that the solvents employed do not affect the polymerization rate of the monomer. Thus, these solvents do not decrease the polymerization rate, and therefore do not mitigate the rapid release of heat over time as the monomer polymerizes.

A category of liquid adhesive bandage has included non-hemostatic alkylsiloxysiloxane-containing polymers admixed with liquid polydimethylsiloxanes (U.S. Pat. Nos. 5,103,812 and 4,987,893) which provide non-stinging, non-irritating coating materials that allow body fluid evaporation and oxygen transport, while protecting the body surface from further contamination and desiccation. In another variation, alkylsiloxysiloxane-containing polymers are admixed with isooctane to provide similar coating properties (U.S. Pat. No. 6,383,502). These coatings have the common disadvantages of loss of adhesion toward hydrated surfaces, loss of adhesion in higher flexibility areas such as knuckles or knees, and no hemostatic capability.

Another category of polymer useful as a liquid adhesive bandage with no hemostatic activity, cycloalkyl methacrylate copolymers, has been found to be soluble in a mixture of liquid polydimethylsiloxanes, iso-octane and isododecane (U.S. Pat. No. 6,358,503).

U.S. Pat. No. 5,214,093 discloses the use of 50% cyanoacrylate monomer, 25% polydimethylsiloxanes and 25% 3-methacryloxypropyltris(trimethylsiloxy)silane (TRIS) monomer as an adhesive formulation for nonsurgical blepheroplasty. This composition raises toxicity and irritation issues as TRIS monomer is applied directly on the eyelid to prepare the surface prior to application of the cyanoacrylate bonding agent.

SUMMARY

The present invention provides a liquid hemostatic coating material that can act as a bandage or dressing to protect or repair wounds and surgical incisions, or to treat damaged or threatened skin or mucosal tissue when applied in liquid form and air dried on a biological surface, forming an adherent, solid protective coating without significant stinging or irritation to the skin, tissues or mucous membranes of the user and where said coating does not adhere to a second surface.

In a preferred embodiment, liquid hemostatic coating materials comprise a cyanoacrylate monomer and a solvent system comprising a volatile hydrophobic liquid, that is non-reactive with the cyanoacrylate monomer prior to application, and that is non-stinging and non-irritating to a user. A hemostatic coating is a coating that arrests the flow of blood. A non-stinging liquid is a liquid that does not cause sharp, sudden, momentary pain when placed upon damaged or undamaged skin, or open wounds, and the like. A non-irritating liquid is a liquid that does not cause inflammation or soreness when placed upon damaged or undamaged skin, or open wounds, and the like. A volatile, hydrophobic liquid is one that is not soluble in water and volatilizes at room or body temperature.

In a preferred embodiment, the cyanoacrylate monomer is present from about 0.1% to about 99.9% by weight, more preferably, the cyanoacrylate monomer is present from about 0.1 to about 95% by weight, and most preferably, the cyanoacrylate monomer is present from about 0.1 to about 90% by weight. Preferably, the non-stinging, non-irritating, volatile non-reactive liquid is present from about 0.1% up to 99.9% by weight, more preferably the volatile non-reactive liquid is present from about 5% up to 99.9% by weight, most preferably from about 10% to 99.9% by weight. The material forms a coating or bandage when applied to a surface or the skin of a user.

In a preferred embodiment, the non-stinging, non-irritating, volatile, non-reactive liquid is a low molecular weight linear or cyclic siloxane. Silicone liquids, which are inorganic/organic hybrids, are noted for their very low critical surface tensions. When a cyanoacrylate monomer is admixed with a siloxane solvent, such as hexamethyldisiloxane, and said solution is applied to a wet surface, the contents of the liquid at the air interface will be predominantly the silicone liquid. This silicone-containing interface thus prevents adhesion of the polymerizing cyanoacrylate to another surface. Furthermore, because of the low surface tension of silicone liquids, the mixture will spread easily over a biological surface in comparison to the application of neat cyanoacrylate, which will have a tendency to bead and not flow. Thus, the incorporation of a siloxane liquid with a cyanoacrylate will lead to more rapid coverage of a damaged area in a shorter time than neat cyanoacrylate.

In another preferred embodiment, the liquid coating materials of this invention comprise a silane-containing polymer, preferably a siloxysilane-containing polymer, a cyanoacrylate monomer, and a solvent system comprising a volatile, non-reactive hydrophobic (non-polar) liquid that is non-stinging and non-irritating to a user. Preferably, the polymer is present from about 0.01% to about 99.5% by weight, more preferably from about 0.5% to about 70% by weight, most preferably from about 1% to about 40%. Additionally, the cyanoacrylate monomer is present from about 0.1% to about 99.5% by weight, more preferably, from about 0.1 to about 70% by weight, most preferably from about 0.5% to about 50%. The non-stinging, non-irritating, volatile, hydrophobic liquid is present from about 0.5% to 99.9% by weight, more preferably about 5% to 99.5% by weight, most preferably from about 10% to about 98.5%. The material forms a coating, bandage or glue in the form of a film when applied to a surface or the skin of a user, wherein said surface does not bond to another surface. The siloxysilane-containing polymer provides for water and oxygen transport through the polymer film that is believed to aid in healing. Without wishing to be bound by theory, the film is in the form of an interpenetrating polymer network, wherein the cyanoacrylate polymer is interdispersed within the siloxysilane polymer.

In a preferred embodiment, when a siloxysilane-containing polymer is present, the siloxysilane-containing polymer comprises at least one vinyl-containing siloxysilane monomer (about 20 to 85 mole %) copolymerized with monomers that, in polymer form, are not reactive with the cyanoacrylate monomer prior to application to the surface. These non-reactive monomers may serve the function of increasing adhesion and cohesion of the polymer. The non-stinging, non-irritating, volatile, non-reactive hydrophobic liquid is preferably a volatile, low molecular weight linear or cyclic siloxane.

In another preferred embodiment, siloxysilane monomers according to claim 5 comprise at least one of:
  3-methacryloyloxypropyltris(trimethylsiloxy)silane,
  3-methacryloyloxypropylpentamethyldisiloxane,
  3-methacryloyloxypropylbis(trimethylsiloxy)methylsilane,
  3-methacryloyloxypropyltris(vinyldimethylsiloxy)silane,
  3-methacryloyloxymethylbis(trimethylsiloxy)(pentamethyldisiloxanyl)silane,
  3-methacryloyloxyethyltris(pentamethyldisiloxanyl)silane,
  methacryloyloxymethylbis(trimethylsiloxy)methylsilane,
  methacryloyloxymethyltris(trimethylsiloxy)silane,
  3-methacryloyloxypropylheptacyclopentyl-T8-silsesquioxane,
  3-methacryloyloxypropylheptaisobutyl-T8-silsesquioxane,
  3-acryloyloxypropylmethylbis(trimethylsiloxy)silane,
  3-acryloyloxypropyltris(trimethylsiloxy)silane,
  3-methacryloyloxypropyl-1,1,1-triphenyl-3,3-dimethyldisiloxane,
  3-methacrylamidopropyltris(trimethylsiloxy)silane,
  3-acrylamidopropyltris(trimethylsiloxy)silane,
  p-vinylphenyltris(trimethylsiloxy)silane,
  p-vinylbenzyltris(trimethylsiloxy)silane,
  vinyloxyethyltris(trimethylsiloxy)silane,
  vinylnonyldimethyl(trimethylsiloxy)silane,
  vinylnonyltris(trimethylsiloxy)silane,
  vinylmethylbis(trimethylsiloxy)silane,
  vinylpentamethyldisiloxane,
  O-(vinyloxyethyl)-N-(tris[trimethylsiloxy]silylpropyl) urethane,
  vinylphenylbis(trimethylsiloxy)silane,
  vinyltris(dimethylsiloxy)silane,
  vinyltris(trimethylsiloxy)silane,
  vinyl-terminated polydimethylsiloxane,
  polydimethylsiloxane monoacrylate,
  polydimethylsiloxane monomethacrylate,
  polymethylphenylsiloxane monoacrylate,
  polymethylphenylsiloxane monomethacrylate, or
  3-acryloyloxypropyltris(polydimethylsiloxanyl)silane.

In another preferred embodiment the non-stinging, non-irritating, volatile, non-reactive liquid is selected from the group having a solubility parameter from 4.9-12.5 $(cal/cm^3)^{1/2}$.

In another preferred embodiment, the non-stinging, non-irritating, volatile, non-reactive liquid is selected from the group having a solubility parameter from 5-10 $(cal/cm^3)^{1/2}$.

In yet another embodiment, the non-stinging, non-irritating, volatile, non-reactive liquid comprises volatile linear and cyclic siloxanes, and volatile polydimethylsiloxanes.

In a preferred embodiment, a coating provides for hemostasis.

In another preferred embodiment, the volatile, non-reactive solvent is an alkane, such as isooctane, octane, neopentane, and the like; volatile fluorocarbons, such as pentafluoropropane, perfluoroheptane, perfluoromethylcyclohexane and the like; or a volatile gas, when used under pressure as a solvent, such as carbon dioxide.

In another preferred embodiment, a coating is provided that adheres to its applied surface but does not allow the applied surface to adhere to another surface.

In another preferred embodiment, a coating is provided that does not generate discomfort through generation of stinging or irritation when the solvent contacts damaged skin or tissue.

In another preferred embodiment, the non-stinging, non-irritating solvent decreases the polymerization rate of the cyanoacrylate monomer, thus decreasing with time the release of its heat of polymerization. The greater the concentration of non-stinging, non-irritating solvent, the greater the reduction in the rate of polymerization and the less heat generated with time.

In another preferred embodiment, a coating is provided that does not generate discomfort through generation of heat from the polymerizing cyanoacrylate monomer, through volatilization of the non-stinging, non-irritating solvent, when said coating is applied to a surface. Alternatively, by decreasing the concentration of the non-stinging solvent, cauterization can be effected if it is desired to reduce or kill microorganisms at a wound site.

In another preferred embodiment, a coating is provided that is adherent to hydrated and/or non-hydrated surfaces.

In another preferred embodiment, a coating is provided that remains adherent to a surface when exposed to external water, soaps, detergents, and skincare products.

In another preferred embodiment, a coating is provided that prevents further microorganism or particulate contamination to skin or mucous membrane wounds or incisions.

In another preferred embodiment, a transparent covering is provided that does not attract or hold dirt and can remain colorless and clear for wound viewing as well as cosmetic attractiveness.

In another preferred embodiment, a coating is provided, that, when applied, controls body fluid loss from an abraded area.

In another preferred embodiment, a polymer film is provided which allows moisture and oxygen transport.

In another preferred embodiment, a polymer film is provided in which medicaments or other active agents may be incorporated for controlled delivery into targeted areas.

In another preferred embodiment, a coating is provided that, after application to a surface, releases from that surface gradually over time without requiring externally applied solvents or other removal methods.

A still further object of this invention is to provide a surgical glue wherein a treated surface will not attach to other surrounding surfaces.

Other aspects of the invention are described infra.

DETAILED DESCRIPTION

The cyanoacrylate monomers, when incorporated into non-stinging, non-irritating, volatile, non-reactive liquids and when polymerized, provide for a fast drying, hemostatic, adherent, non-stinging and non-irritating liquid adhesive coating or bandage that inhibits adhesion of two surfaces to each other. In the absence of the non-stinging, non-irritating, volatile, non-reactive liquid, considerable discomfort is caused by a volatile organic solvent coming in contact with damaged skin as well as heat generation due to the rapid polymerization of the cyanoacrylate monomer. The non-stinging, non-irritating, volatile, non-reactive liquid of the coating formulation is believed to evaporate during the polymerization of the cyanoacrylate monomer because of its low heat of vaporization, thus removing the heat of polymerization from the applied surface. Further, when said non-stinging, non-irritating, volatile solvent is a siloxane solvent, such as hexamethyldisiloxane, such compounds that have a low heat of vaporization (46 cal/g) generate rapid coating formation, and hence relief to a user, because of the rapid removal of the solvent.

When a siloxysilane-containing polymer is added to the above, a continuous film is introduced that provides greater skin coverage and adhesion. The siloxysilane polymer also aids in moisture and oxygen transport through the film to the damaged skin. These hemostatic coating materials are particularly useful on slowly bleeding or exudating wounds.

This liquid hemostatic coating can comprise medicants or other active materials that can be gradually released onto targeted areas, if desired.

The liquid hemostatic coatings, comprised of the cyanoacrylate monomer and non-stinging, non-irritating, volatile solvent, including incorporation of a siloxysilane-containing polymer, are useful for protecting or treating skin, nails, tissues, organs and mucous membranes, e.g. bleeding injuries, surgical sites, skin ulcers, cuts, abrasions, incisions, cold sores, blisters, rashes, abraded gums and other oral surfaces, hemorrhoids and abraded body areas, and other mucosal membrane incisions and wounds. The liquid adhesive materials may also be used as surgical glues. They also find application in pediatric care and veterinary care.

As the liquid hemostatic bandages are non-stinging and non-irritating and instantly cover exposed nerve endings, pain is reduced immediately. The bandages remain adherent to the skin/mucosal surface for up to 2 days or more, relieving pain and gradually lifting off without creating damage or irritation.

Compositions

Preferred cyanoacrylate monomers that may be used in this invention include readily polymerizable alpha-cyanoacrylates, including alkyl cyanoacrylates, aryl cyanoacrylates, alkoxyalkyl cyanoacrylates, such as n-butyl cyanoacrylate, 2-octyl cyanoacrylate, ethyl cyanoacrylate, methyl cyanoacrylate, n-dodecyl cyanoacrylate, phenyl 2-cyanoacrylate, methoxyethyl 2-cyanoacrylate, and the like. The composition may be composed of one or more polymerizable cyanoacrylate monomers. The preferred cyanoacrylates are n-butyl cyanoacrylate and 2-octyl cyanoacrylate, with n-butyl cyanoacrylate being the most preferred.

Preferably, the cyanoacrylate monomer is present from about 0.1% to about 99.9% by weight, more preferably, the cyanoacrylate monomer is present from about 0.1 to about 95% by weight, and most preferably, the cyanoacrylate monomer is present from about 0.1 to about 90% by weight.

The cyanoacrylate monomers of the invention are incorporated into a solvent system comprising non-stinging, non-irritating, volatile, non-reactive liquids, preferably having a solubility parameter from about 4.9-12.5 $(cal/cm^3)^{1/2}$, preferably from about 5-8 $(cal/cm^3)^{1/2}$. The non-stinging, non-irritating solvent system can comprise volatile liquid siloxanes, such as hexamethyldisiloxane (HMDS), octamethylcyclotetrasiloxane, decamethylcyclopentasiloxane, octamethyltrisiloxanes and the like. The most preferred non-stinging, non-burning, volatile solvent system is hexamethyldisiloxane. Other volatile solvents, including volatile alkanes, such as isooctane, octane, neopentane and the like; volatile fluorocarbons, such as pentafluoropropane, perfluoroheptane, perfluoromethylcyclohexane and the like; or a volatile gas, such as carbon dioxide, can also be employed, each with varying degrees of user discomfort.

Preferably, the non-stinging, non-irritating, volatile non-reactive liquid is present from about 0.1% up to 99.9% by weight, more preferably, the volatile non-reactive liquid is present from about 5% up to 99.9% by weight, and most preferably from about 10% to 99.9% by weight.

The use of these non-stinging, non-irritating, volatile, non-reactive liquids, simply or in combination, as the primary liquid phase of the liquid coating provides for rapid drying and less coating tackiness during drying. Notably, the use of these volatile non-reactive liquids inhibits adhesion of two surfaces to each other while allowing for good adhesion of the coating to its applied surface. During evaporation, the volatile non-reactive liquid solvent, having a low surface energy, is predominantly found on the air interface or "top" surface of the coating, hence inhibiting the cyanoacrylate from reaching the surface of the liquid coating and preventing an adherent bond to other surfaces that may be present.

Additionally, the use of these non-stinging, non-irritating, volatile, non-reactive liquids, simply or in combination, allows for the liquid adhesive coating that contains reactive cyanoacrylates to be applied by painting, spraying, pumping, dipping or the like.

In the presence of a siloxysilane-containing polymer, the siloxysilane-containing polymer component of this invention preferably comprises addition polymerizable siloxysilanes, which polymers are water vapor and oxygen permeable, and which monomers may be copolymerized with other noncyanoacrylate reactive monomers to form co- or multi-polymers. Water vapor and oxygen permeability, which are provided by the siloxysilane-containing polymer component, are important for wound care and prevention of skin/tissue degradation. The water vapor permeability prevents desiccation and allows for removal of body waste (sweat), while the oxygen permeability may aid in wound healing.

The siloxysilane monomers of the siloxysilane polymers include:
3-methacryloyloxypropyltris(trimethylsiloxy)silane (TRIS),
3-methacryloyloxypropylpentamethyldisiloxane,
3-methacryloyloxypropylbis(trimethylsiloxy)methylsilane,
3-methacryloyloxypropyltris(vinyldimethylsiloxy)silane,
3-methacryloyloxymethylbis(trimethylsiloxy)(pentamethyldisiloxanyl)silane,
3-methacryloyloxyethyltris(pentamethyldisiloxanyl)silane,
methacryloyloxymethylbis(trimethylsiloxy)methylsilane
methacryloyloxymethyltris(trimethylsiloxy)silane
3-methacryloyloxypropylheptacyclopentyl-T8-silsesquioxane
3-methacryloyloxypropylheptaisobutyl-T8-silsesquioxane
3-acryloyloxypropylmethylbis(trimethylsiloxy)silane,
3-acryloyloxypropyltris(trimethylsiloxy)silane,
3-methacryloyloxypropyl-1,1,1-triphenyl-3,3-dimethyldisiloxane,
3-methacrylamidopropyltris(trimethylsiloxy)silane,
3-acrylamidopropyltris(trimethylsiloxy)silane,
p-vinylphenyltris(trimethylsiloxy)silane
p-vinylbenzyltris(trimethylsiloxy)silane,
vinyloxyethyltris(trimethylsiloxy)silane,
vinylnonyldimethyl(trimethylsiloxy)silane,
vinylnonyltris(trimethylsiloxy)silane,
vinylmethylbis(trimethylsiloxy)silane,
vinylpentyldisiloxane,
O-(vinyloxyethyl)-N-(tris[trimethylsiloxy]silylpropyl)urethane,
vinylphenylbis(trimethylsiloxy)silane,
vinyltris(dimethylsiloxy)silane,
vinyltris(trimethylsiloxy)silane,
vinyl-terminated polydimethylsiloxane,
polydimethylsiloxane monoacrylate,
polydimethylsiloxane monomethacrylate,
polymethylphenylsiloxane monoacrylate,
polymethylphenylsiloxane monomethacrylate,
3-acryloyloxypropyltris(polydimethylsiloxanyl)silane, and the like.

These siloxysilane monomers, as polymerized, provide for solubility in the non-stinging, non-irritating, volatile, non-reactive, hydrophobic solvent systems of choice.

Other addition polymerizable monomers may also be incorporated into the siloxysilane-containing polymers of this invention to modify adhesion, cohesion, flexibility, toughness, for instance. Examples of these other monomers are methyl methacrylate, methyl acrylate, tetrahydrofurfuryl methacrylate, cyclohexyl acrylate, tetrahydrofurfuryl acrylate, n-lauryl acrylate, n-lauryl methacrylate, 2-phenoxyethyl acrylate, 2-phenoxyethyl methacrylate, isodecyl acrylate, isodecyl methacrylate, isooctyl acrylate, isooctyl methacrylate, isobornyl acrylate, isobornyl methacrylate, benzyl acrylate, benzyl methacrylate, 2-butoxyethyl acrylate, n-butyl acrylate, n-butyl methacrylate, ethyl acrylate, ethyl methacrylate, dimethyl itaconate, di-n-butyl itaconate, 2-ethylhexyl acrylate, 2-ethylhexyl methacrylate, furfuryl methacrylate, n-hexyl acrylate, n-hexyl methacrylate, isobutyl acrylate, isobutyl methacrylate, isopropyl methacrylate, pentyl acrylate and methacrylate, 2-pentyl acrylate and methacrylate, 3-pentyl acrylate and methacrylate, 2-methyl-1-butyl acrylate and methacrylate, 1-methyl-1-butyl acrylate and methacrylate, 1-methyl-1-pentyl acrylate and methacrylate, 2-methyl-1-pentyl acrylate and methacrylate, 3-methyl-1-pentyl acrylate and methacrylate, 2-ethyl-1-butyl acrylate and methacrylate, 2-ethyl-1-hexyl acrylate and methacrylate, 3,5,5-trimethyl-1-hexyl acrylate and methacrylate, 3-heptyl acrylate and methacrylate, decyl acrylate and methacrylate, dodecyl acrylate and methacrylate, α-methylstyrene, p-t-butylstyrene, 4-methoxystyrene, n-octadecyl acrylate, n-octadecyl methacrylate, 2-phenylethyl acrylate, 2-phenylethyl methacrylate, n-tridecyl methacrylate, vinyl benzoate, vinyl naphthalene, and the like. In addition, fluorinated siloxanes, fluorinated itaconates, fluorinated methacrylates or acrylates, such as hexafluoroisopropyl methacrylate, can be used. Furthermore, dienes such as butadiene or isoprene and their oligomers, derivatized or not, can be used.

Any hydrophobic or hydrophilic polymerizable monomer can be used as long as the resulting copolymer has desired oxygen and water vapor permeability, desired adhesion to its applied surface, desired cohesion, and non-reactivity with the cyanoacrylate monomer (until application to the surface) that is a component of the liquid hemostatic composition of this invention.

The siloxysilane polymers can be obtained by free radical polymerization of the monomers utilized, including thermal free radical polymerization, redox free radical polymerization, photoinitiated free radical polymerization, and living radical polymerization. If desired, block copolymers can be prepared by living radical polymerization or living anionic polymerization. Thermal free radical polymerization is preferred, and an azo free radical initiator is most preferred, such as 2,2'-azobis(2-methylbutyronitrile), with polymerization done between 70-75° C. in the presence of nitrogen.

The siloxysilane-containing polymers of this invention increase coating flexibility and durability of the applied adhesive coating. Coating flexibility allows use of the coatings of this invention on flexible areas of the body, e.g., knees, knuckles and elbows, as the coating can comfortably flex with body movement while retaining coating integrity. Durability of the dried coating on its applied surface for at least 2 days is desirable.

Non-volatile liquid siloxanes, such as derivatives of polysiloxanes and the like, may also be used with or without the siloxysilane-containing polymer of this invention for increased flexibility and durability of the applied adhesive coating.

The polymer and monomer components of the invention are incorporated into a solvent system comprising volatile hydrophobic liquids, preferably having a solubility parameter between about 5.0-8.0 $(cal/cm^3)^{1/2}$. Hydrophobic liquids are defined for the purposes of this invention as being non-water compatible. The solvent system comprises volatile liquid silicones, such as hexamethyldisiloxane (HMDS), octamethylcyclotetrasiloxane, decamethylcyclopentasil-oxane, octamethyltrisiloxanes and the like. The solubility parameter of hexamethyldisiloxane is reported to be 5.7 $(cal/cm^3)^{1/2}$ and that of octamethylcyclotetrasiloxane as 5.4 $(cal/cm^3)^{1/2}$ (see U.S. Pat. No. 5,103,812, col. 6). The preferred solvent system is hexamethyldisiloxane. Other volatile solvents, including volatile alkanes, such as isooctane, octane, neopentane and the like; volatile fluorocarbons, such as pentafluoropropane, perfluoroheptane, perfluoromethylcyclohexane and the like; or a volatile gas, such as carbon dioxide, can also be employed, each with varying degrees of user discomfort.

Polymer coatings of the invention cast from liquids containing good solvents with solubility parameters of between about 9 to 10 (cal/cm³)$^{1/2}$ will function, but are generally slow to dry and remain tacky for extended periods.

The use of these non-stinging, non-irritating, volatile, hydrophobic liquids, simply or in combination, as the primary liquid phase of the liquid hemostatic coating provides for rapid drying and less coating tackiness during drying. Notably, the use of these volatile hydrophobic liquids inhibits adhesion of two surfaces to each other while allowing for good adhesion of the coating to its applied surface for wound protection and repair. During evaporation, the volatile hydrophobic liquid is predominantly found on the air interface or "top" surface of the coating because of its low surface energy with air, hence inhibiting the cyanoacrylate monomer from reaching this surface and reacting to form an adherent bond to other surfaces that may be present.

The liquid hemostatic coating material, composed of the siloxysilane-containing polymer, cyanoacrylate monomer and solvent, is useful for protecting or treating skin, tissues, organs, nails, hydrated tissues and mucous membranes, e.g. bleeding injuries, surgical site, skin ulcers, cold sores, cuts, rashes, abrasions, incisions and blisters, abraded gums and other oral surfaces, hemorrhoids and abraded body areas, and other mucosal membrane incisions and wounds. Said coating materials also find application in pediatric care and veterinary care.

As the liquid hemostatic bandage is non-stinging and non-irritating and instantly covers exposed nerve endings, pain is reduced immediately. The bandage remains adherent to the skin/mucosal surface for up to 4 days, relieving pain and gradually lifting off without creating damage or further irritation.

Normal unabraded skin loses moisture vapor at an average rate of 200 g/m²/day in most areas; the palms of the hand and soles of the feet respire at an average of 500 g/m²/day. The siloxysilane-containing polymer liquid hemostatic materials of this invention have moisture vapor transmission rates of 100 to 200 g/m²/day depending on protective film thickness (0.001-0.005 inches), thus preventing both dehydration of the wounded area and occlusion of body fluids.

Depending on the particular requirements of the user, the hemostatic compositions of this invention can be applied by known means, such as with a spray, pump, swab, rod, sterile brush or medicine dropper. However, in many situations a pump dispensing package is preferred for the hemostatic composition of this invention. Other modes of application are exemplified in U.S. Pat. No. 5,928,611, incorporated by reference herein in its entirety.

The stability, and thus the shelf-life, of some monomeric cyanoacrylate hemostatic, adhesive compositions can be further enhanced and extended through careful regulation of the packaging, wherein neither the packaging material nor any additives cause the spontaneous polymerization of the cyanoacrylate. In certain instances, however, acidic inhibitors, such as sulfur dioxide, are present in the cyanoacrylate monomers to prevent spontaneous polymerization.

Other Variations of the Compositions

Other substances may be added to the liquid material or formulation for additional plasticization, improved adhesion, or rheology control, and the like, with the proviso that they do not induce spontaneous polymerization of the cyanoacrylate monomer.

Typical plasticizer/adhesion promoters are dibutylphthalate, acetyl tributyl citrate, sucrose acetate isobutyrate, sucrose benzoate, acetyltriethyl citrate, mineral oil, decamethylcyclopentasiloxane, octamethylcyclotetrasiloxane, poly(methyphenylsiloxane), butyl glycolate and others. The plasticizing agent preferably contains little or no moisture and should not significantly affect the polymerization of the cyanoacrylate monomer. Suitable plasticizers include polymeric plasticizers, such as poly(ethylene glycol) (PEG) esters and capped PEG esters or ethers, polyester glutarates and polyester adipates. Other compositions are exemplified by U.S. Pat. Nos. 5,259,835 and 5,328,687; 5,981,621; 6,143,352; 6,565,840; 6,010,714; 6,217,603; and 5,928,611, all incorporated by reference herein in their entirety.

Typical rheology additives that may be added to the liquid material or formulation are fumed silica, bentonite and other clay derivatives, and the like, provided that they do not cause polymerization of the cyanoacrylate monomer.

The composition may optionally also include thickeners. Suitable thickeners include, for example, polycyanoacrylates, polycaprolactone, polyorthoesters, polyalkyl acrylates, copolymers of alkyl acrylate and vinyl acetate, poly(alkyl methacrylate)s, and copolymers of alkyl methacrylates and butadiene. Examples of alkyl methacrylates and acrylates are poly(methyl methacrylate), poly(2-ethylhexyl methacrylate) and poly(2-ethylhexyl acrylate), also poly(butyl methacrylate) and poly(butyl acrylate), also copolymers of various acrylate and methacrylate monomers, such as poly(butyl methacrylate-co-methyl acrylate).

The composition may also optionally include at least a natural or synthetic rubber or thermoplastic elastomer to impart impact resistance. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties by reference herein.

The compositions may also include pH modifiers to control the rate of degradation of the resulting polymer, as disclosed in U.S. Pat. No. 6,143,352, the entire disclosure of which is hereby incorporated by reference herein in its entirety.

To improve the cohesive strength of adhesives formed from the compositions of this invention, difunctional monomeric crosslinking agents in concentration of less than 2 wt % of the mixture may be added to the monomer compositions of this invention. Such crosslinking agents are known such as in U.S. Pat. No. 3,940,362.

The compositions of this invention may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593, the disclosure of which is incorporated by reference herein in its entirety. Examples of suitable colorants as described in U.S. Pat. No. 5,981,621 include 1-hydroxy-4-[4-methylphenylamino]-9,10-anthracenedione (FD+C violet No. 2); disodium salt of 6-hydroxy-5-[(4-sulfophenyl)oxo]-2-naphthalenesulfonic acid (FD+C Yellow No. 6); 9-(o-carboxyphenyl)-6-hydroxy-2,4,5,7-tetraiodo-3H-xanthen-3-one, disodium salt, monohydrate (FD+C Red No. 3); and the like.

The compositions of the present invention may also include one or more polymerization stabilizers for the cyanoacrylate monomer, preferably both at least one anionic vapor phase stabilizer and at least one anionic liquid phase stabilizer. Such stabilizing agents may also include mixtures of anionic stabilizing agents and radical stabilizing agents. These stabilizing agents may inhibit premature polymerization. Suitable stabilizers may include those listed in U.S. Pat. No. 6,183,593, the disclosure of which is incorporated by reference herein in its entirety. Furthermore, certain stabilizers may also function as anti-fungal agents.

Medicants

Medicants may be incorporated into the liquid or solid film bandages for ready or continual release from the liquid hemostatic adhesive material components, which allow incorporation of a variety of medicants, and which are long lasting and permeable. The addition of a medicant should not facilitate spontaneous polymerization of the cyanoacrylate monomer prior to its application to the surface of a user. Examples of useful medicants are fungicides, antibacterial agents, antiviral agents, cell growth factors, antibiotics, anti-inflammatory agents, anti-itch agents, anti-infective agents, antitumor agents, blood pressure and heart regulators, steroids and many more.

Tissue growth-promoting agents may be incorporated or suspended into the liquids of this invention to encourage production of new tissue, adhesion of new tissue, cell migration, etc., provided that they do not cause the spontaneous polymerization of the cyanoacrylate monomer. For example, cytokines, such as epidermal growth factor, transforming growth factor (TGF)-alpha, TGF-beta and the like, incorporated into the liquid adhesive film bandage of this invention may facilitate the re-growth of wounded areas.

As noted above, a biological component may, optionally, be incorporated within the bandage material. When present, the biological component can be selected from among a variety of effectors that, when present at the site of injury, promote healing and/or regeneration of the affected tissue. In addition to being compounds or agents that actually promote or expedite healing, the effectors may also include compounds or agents that prevent infection (e.g., antimicrobial agents and antibiotics), compounds or agents that reduce inflammation (e.g., anti-inflammatory agents), compounds that prevent or minimize adhesion formation, such as oxidized regenerated cellulose, hyaluronic acid, and compounds or agents that suppress the immune system (e.g., immunosuppressants).

Suitable effectors for use with the bandages of the present invention can also include sources of growth factors, such as for example, platelets. Platelets are normally found in the blood and play a role in hemostasis and wound healing. During clot formation, the platelets become activated and release growth factors such as PDGF, TGF-β, VEGF, and IGF. Platelets can be separated from blood using techniques such as centrifugation. When platelet rich plasma is combined with an activator, a platelet clot is created. An activator can be, but is not limited to, thrombin, adenosine diphosphate (ADP), collagen, epinephrine, arachidonic acid, Ristocetin, and combinations thereof.

Activators useful with this invention may have secondary therapeutic actions that contribute to the healing process. For example, Ristocetin not only stimulates platelet aggregation, but is also an antibiotic. It acts by inhibiting bacterial cell wall formation and is most efficacious against actively growing bacteria. Since any invasive procedure has the potential to induce infection, the benefits of including Ristocetin are two fold: its presence stimulates clot formation while also providing a prophylactic action against infection. Gram positive bacteria such as staphylococcus, known to cause hospital-borne infection are susceptible to treatment with Ristocetin.

The biological additives can either be dissolved and compatible in the liquid hemostatic adhesive formulation or can remain suspended, provided that they do not cause polymerization of the cyanoacrylate monomer.

Other Applications

The liquid hemostatic adhesive coatings of this invention could be used for applications other than human or animal body care. For instance, the coatings could be used as a membrane, or part thereof, and, as such, could contain conductive additives or other additives to enhance the membrane effectiveness. The coatings incorporating a mildewcide could be used to protect grout in tile surfaces. Other types of active agents which may be desirable to incorporate include perfumes, plant growth regulators, plant insecticides, UV and IR absorbers, etc. The liquid adhesive coatings of this invention could also be used to detect latent fingerprint residues or other residues.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the embodiments illustrated, but instead should be determined with reference to the appended claims along with their full scope of equivalents.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

The preparation of the siloxysilane polymers are illustrated below:

Poly(3-methacryloyloxypropyltris(trimethylsiloxy)silane (TRIS)-co-methyl methacrylate-co-isooctyl acrylate (PSS1)—This terpolymer was obtained by the procedure represented by U.S. Pat. No. 5,103,812, Example 26.

Poly(3-methacryloyloxypropyltris(trimethylsiloxy)silane (TRIS)-co-methyl methacrylate) (PSS2)—This copolymer was obtained by polymerization of its monomer components in a 25 ml reaction vessel charged with 6 g ethyl acetate, 1.8 g (0.004 mol) TRIS, 0.2 g (0.002 mol) methyl methacrylate, and 0.04 g 2,2'-azobis(2-methylbutanenitrile). The polymerization was run for 21 hours at 72-75° C. The polymer was precipitated into methanol and dried at 50° C.

Poly(3-methacryloyloxypropyltris(trimethylsiloxy)silane (TRIS)-co-n-butyl methacrylate) (PSS3). This copolymer was obtained by polymerization of its monomer components in a 25 ml reaction vessel charged with 6 g ethyl acetate, 1.8 g (0.004 mol) TRIS, 0.2 g (0.0014 mol) n-butyl methacrylate and 0.04 g 2,2''-azobis(2-methylbutanenitrile). The polymerization was run for 21 hours at 72-75° C. The polymer was precipitated into methanol and dried at 50° C.

Example 1

Butyl Cyanoacrylate Tested with Disiloxane Liquid n-Butyl cyanoacrylate (BCA) was mixed into hexamethyldisiloxane (HMDS) at about a one to one volume ratio. When this formulation was pipetted onto a glass slide and covered with another glass slide, the cyanoacrylate polymerized as verified by formation and adhesion of the polymer onto the first applied glass slide. The polymerized cyanoacrylate containing HMDS did not provide adequate adhesion to a second covering slide to prevent the two glass slides from being readily pulled apart.

Additionally, a test was conducted for the rate of polymerization as a function of solvent concentration in order to assess the time interval for heat generation upon the polymerization of the cyanoacrylate monomer. The mixture included n-butyl cyanoacrylate in the presence and absence of hexamethyldisiloxane. According to U.S. Pat. No. 6,010,714, which utilized a heat dissipating agent in the presence of a cyanoacrylate monomer, the heat dissipating agent did not affect the rate of polymerization. Utilizing a glass slide containing BCA with no HMDS as the control, polymerization of this neat system occurred in 25 seconds. When a 20% BCA solution in HMDS was studied, utilizing the same amount of BCA as in the control, polymerization occurred in 40 seconds, and decreased the polymerization rate by 60%. Further, when a 5% solution of BCA in HMDS was studied, polymerization occurred in 89 seconds, and this dilution decreased the polymerization rate by 256%. Thus, the addition of the non-stinging, non-irritating volatile hexamethyldisiloxane solvent caused polymerization of the cyanoacrylate to occur at a slower rate than that reported by U.S. Pat. No. 6,010,714, allowing the heat of polymerization to be more evenly dissipated. It was also found that the addition of the HMDS solvent, which has a low critical surface tension, allowed the BCA mixture to flow readily over the glass surface, whereas the BCA by itself tended to bead because of its higher critical surface tension. The use of the HMDS would thus facilitate rapid coverage of a wound site.

Examples 2-6

Butyl Cyanoacrylate Tested with Disiloxane Liquid n-Butyl cyanoacrylate was mixed into hexamethyldisiloxane at various concentrations by weight. Hemostasis ability was tested by pipetting 5 µl of pork blood on a microscope slide immediately followed by pipetting 5 µl of the liquid hemostatic composition directly on top of the blood droplet. In addition to hemostasis testing, adhesion of two surfaces that are pressed together in the presence of the compositions was tested. 5 µl of the compositions was pipetted onto a glass slide, allowed to dry/react for about 10 seconds, and then another glass slide was pressed onto the coated first slide. After about 1 minute, force was applied to the glass slides to pull them apart.

In Examples 2 and 3 with BCA concentrations 30% and less, the BCA adhered well to its applied glass surface but did not adhere to a second glass surface that was pressed onto the first applied glass surface. Examples 4-6 demonstrate the inherent capability of BCA to adhere two surfaces to each other when inadequate amounts of the non-stinging, non-irritating, volatile, non-reactive liquid are present, that is, at concentrations of BCA of 50% and greater.

| Ex | BCA/HMDS (wt %) | Hemostasis Ability | Adhesion to two glass surfaces |
|---|---|---|---|
| 2 | 10 | coagulation | no |
| 3 | 30 | coagulation | no |
| 4 | 50 | explosive coagulation | yes |
| 5 | 80 | explosive coagulation | yes |
| 6 | 100 (no HMDS) | explosive coagulation | yes |

Examples 7-11

Testing of octyl cyanoacrylate/polysiloxysilane solution (SOL1)

2-Octyl cyanoacrylate (OCA) was mixed with a solution containing poly(3-methacryloyloxypropyltris(trimethylsiloxy)silane-co-methyl methacrylate-co-isooctyl acrylate) (PSS1), polyphenylmethylsiloxane and hexamethyldisiloxane. This solution shall be abbreviated as SOL1 (solution one) in the following references. The resultant liquid adhesives were cast onto Teflon™ sheet and evaluated for film forming characteristics as shown in the following chart.

| Ex | OCA/SOL1 (grams) | OCA/SOL1 (solids, by parts) | Film Integrity as cast on Teflon ™ |
|---|---|---|---|
| 7 | 0.08/0.91 | 1:1 | film contracts, forms holes |
| 8 | 0.07/0.14 | 10:1 | film contracts, forms discreet clumps |
| 9 | 0.02/2.19 | 1:10 | film conforms to Teflon ™ |
| 10 | 0.02/1.04 | 1:5 | film contracts slightly, conforms to Teflon ™ |
| 11 | 0.00/1.2 | 0:1 | film conforms to Teflon ™ |

With higher concentrations of polysiloxysilane to 2-octyl cyanoacrylate than 1:1 (comparison of Example 7 with Examples 9 and 10), the film forming characteristics on Teflon™ of the solution are good. The dried solutions conform to the substrate and form a continuous film. Example 11 illustrates the coating of solution 1 by itself.

Examples 12-16

Testing of butyl cyanoacrylate/polsiloxysilane solution (SOL1)

n-Butyl cyanoacrylate (BCA) was mixed into the polysiloxysilane-co-methyl methacrylate-co-isooctyl acrylate terpolymer solution (SOL1) at four different weight percentages based on percent solids. These liquid adhesive compositions were then tested.

Hemostasis ability was tested by pipetting 5 µl of beef blood on a microscope slide immediately followed by pipetting 15 µl of the liquid adhesive composition directly on top of the blood droplet. A "yes" result indicates the blood droplet coagulated in the presence of the added coating.

Adhesion to skin was tested by pipetting 10 µl of the liquid adhesive composition onto a human forearm which had previously been stained with blue food coloring dye. The blue food coloring dye is water soluble and, hence, is readily washed off upon exposure to water (shower, washing dishes, etc). The liquid adhesive compositions, which were applied on top of the dried blue food coloring, prevent washing off of the blue food coloring. Once the liquid adhesive compositions are no longer present on the forearm, the blue food coloring is readily washed off. Adhesion of the liquid adhesives was determined by the presence of blue food coloring dye.

| Ex | BCA to SOL1 (wt % of solids) | Hemostasis Ability | Forearm Adhesion (days) |
|---|---|---|---|
| 12 | 0 | no coagulation | 4 |
| 13 | 9 | coagulated top surface of blood | 3 |

-continued

| Ex | BCA to SOL1 (wt % of solids) | Hemostasis Ability | Forearm Adhesion (days) |
|---|---|---|---|
| 14 | 20 | coagulated more blood | 4 |
| 15 | 30 | instant coagulation | 4 |
| 16 | 100 | explosive coagulation | 2 |

With this series of tests, Example 15 provided good results with forearm adhesion of 4 days and instant blood coagulation. Examples 13 and 14 are also useful as liquid adhesive bandages with gentle hemostasis requirements. It should be noted that n-butyl cyanoacrylate, by itself (Example 16), coagulates blood explosively with considerable burning and remains intact on human forearm skin for only 2 days. For solution 1 with no BCA, no hemostasis was observed.

Examples 17-20

Aging Studies n-Butyl cyanoacrylate or 2-octyl cyanoacrylate was mixed into the polysiloxysilane solution (SOL1) and placed into a container which was non-reactive with the cyanoacrylates. Various weight percentages of the cyanoacrylate (CA) monomer to the polysiloxysilane were evaluated for longer term compatibility and stability of the cyanoacrylate monomers. The mixed solutions were held at room conditions (20° C.) for an extended period of time and tested at Day 1, Month 2, and Month 5 by pipetting a 10 µl drop from each of the solutions onto a drop of beef blood. Hemostasis ability was determined by whether or not the beef blood clotted upon contact with the mixed solution. Skin adhesion was determined by pipetting 15 µl of each of the mixed solutions, after they had been stored for 5 months at 20° C., onto a human forearm.

| Ex | CA/SOL1 (wt % of solids) | Hemostasis Ability | | | Skin Adhesion Ability |
|---|---|---|---|---|---|
| | | Day 1 | Month 2 | Month 5 | Month 5 |
| 17 | 16 wt % BCA | yes | yes | yes | 7 days |
| 18 | 6.5 wt % BCA | yes | yes | yes | 7 days |
| 19 | 16 wt % OCA | yes | no | no | 7 days |
| 20 | 6.5 wt % OCA | yes | no | no | 6 days |

Examples 17 and 18 were stable for at least 5 months of aging as observed by continued hemostasis capability and skin adhesion remaining high for 7 days duration.

Examples 21-25

MVTR Testing n-Butyl cyanoacrylate or 2-octyl cyanoacrylate was mixed into the polysiloxysilane solution (SOL1) and tested for moisture vapor transmission rate (MVTR) and dirt pick-up.

Moisture vapor transmission rate was determined by the rate water vapor passed through 1.5-2.7 mil thick films over a period of three days.

Dirt pick-up was determined by pipetting 0.25 µl of liquid adhesive onto a glass slide, drying the adhesive followed by dipping the slide into topsoil and waving it back and forth several times. The slides were then examined under a microscope for dirt particle pick-up.

Burst strength was determined by casting films of the liquid adhesives in Mason jar bands to produce dried film thickness between 1.5 and 3 mils. Weights were deposited on top of each the films until the film cracked or broke. The higher the weight load required for burst, the higher the cohesive strength of the film. Burst strength (cohesive strength) was increased by 50% with the addition of BCA to the polysiloxysilane (comparison of Examples 21 and 22 with Example 25) due, at least in part, to formation of an interpenetrating polymer network.

| Ex | CA/SOL1 (% of solids) | MVTR (grams/meter²/day) | Dirt pick-up (particle number) | Burst Strength (grams) |
|---|---|---|---|---|
| 21 | 16 wt % BCA | 192 | 37 | 318 |
| 22 | 6.5 wt % BCA | 142 | | 300 |
| 23 | 16 wt % OCA | 100 | | |
| 24 | 6.5 wt % OCA | 104 | | |
| 25 | 0 wt % BCA | 164 | 73 | 200 |

Dirt pick-up is substantially reduced by the addition of BCA to the polysiloxysilane solution (SOL1) (Examples 21 and 25). Moisture vapor transmission rates (MVTR) of Examples 21-24 remain in the same range as Example 25, the polysiloxysilane by itself. The polysiloxysilane (PSS1) is known for its good moisture vapor transmission rate and, hence, its acceptability as a liquid adhesive bandage. Such a product is sold commercially as Nexcare Spray Liquid Bandage by 3M Consumer Health Care, St. Paul, Minn. 55144-1000. Therefore, it is a positive result that the MVTRs remain high with the cyanoacrylate-containing compositions of this invention.

Examples 26-28

Hemostasis and Adhesion Testing

Adhesion of two surfaces that are pressed together in the presence of the compositions was tested in the following manner. 15 µl of the compositions was pipetted onto a glass slide, allowed to dry/react for about 10 seconds, and then another glass slide was pressed onto the coated first slide. After about 5 minutes, force was applied to the glass slides to pull them apart. The same procedure was used with human fingers except only 5 µl of the compositions was tested. Hemostasis ability testing was conducted as in Examples 17-20.

Examples 27 and 28 contain the non-stinging, non-irritating, volatile hydrophobic liquid HMDS, hence, preventing adhesion of two surfaces. Whereas, example 26 does not contain the volatile hydrophobic liquid and adhesion to two surfaces does occur.

| Ex | BCA (% of solids) | Hemostasis Ability | Adhesion of two surfaces | |
|---|---|---|---|---|
| | | | Glass | Human fingers |
| 26 | 100% BCA | explosive coagulation | yes | yes |
| 27 | 32% BCA/SOL1 | coagulation | no | no |
| 28 | 16% BCA/SOL1 | coagulation | no | |

Examples 29-33

Hemostasis and Adhesion Testing n-Butyl cyanoacrylate was mixed into the polysiloxysilane solution (SOL1) and was further tested for hemostasis ability and adhesion with a broader range of formulations containing larger quantities of BCA in relation to the polysiloxysilane solution. Hemostasis ability and adhesion to two surfaces testing was conducted as in Examples 17-20 and Examples 26-28.

| | | Adhesion of two surfaces | |
|---|---|---|---|
| Ex | BCA (% of solution by wt) | Hemostasis Ability | Glass | Human fingers |
| 29 | 10% BCA/SOL1 (50% BCA by % solids) | coagulation | no | no |
| 30 | 25% BCA/SOL1 | coagulation | slight | no |
| 31 | 30% BCA/SOL1 | coagulation | slight | no |
| 32 | 40% BCA/SOL1 | explosive coagulation | moderate | |
| 33 | 50% BCA/SOL1 | explosive coagulation | yes | |

Compositions containing 40% BCA or lower (Example 29-32) provided good blood coagulation while inhibiting adhesion of glass or human fingers to each other. At higher BCA loadings, explosive blood coagulation occurred and glass surfaces were adhered together (such as Example 33), which probably indicates human skin and tissue surfaces would also adhere together if inadvertently touching the composition.

Examples 34-38

Testing of cyanoacrylate/polsiloxysilane solution (SOL2)

n-Butyl cyanoacrylate (BCA) was mixed in various portions with a solution containing poly(3-methacryloyloxypropyltris(trimethylsiloxy)silane-co-methyl methacrylate) (PSS2) and hexamethyldisiloxane. This polysiloxysilane solution shall be abbreviated as SOL2 (solution two) in the following references. The formulations were tested as follows.

Tack was determined by rubbing an index finger lightly over dried polymer coating on glass slide and rating on a scale from 0 to 5 (0=slippery, 1=smooth, 2=smooth with slight resistance, 3=resistance, 4=resistance with slight stickiness, 5=sticky).

Hemostasis ability was tested by pipetting 5 µl of beef blood on a microscope slide immediately followed by pipetting 5 µl of the liquid hemostatic adhesive composition directly on top of the blood droplet. A "yes" result indicates the blood droplet coagulated in the presence of the added hemostatic composition.

Adhesion to skin was tested by pipetting 10 µl of the liquid hemostatic adhesive composition onto a human forearm that had previously been stained with yellow food coloring dye. The yellow food coloring dye is water soluble and, hence, is readily washed off upon exposure to water (shower, washing dishes, etc). The liquid hemostatic adhesive composition, which was applied on top of the dried yellow food coloring, prevents washing off of the yellow food coloring. Once the liquid hemostatic adhesive composition is no longer present on the forearm, the yellow food coloring is readily washed off. Adhesion of the hemostatic composition was determined by the presence of yellow food coloring dye.

| Ex | BCA to SOL2 (wt % of soln.) | Tack | Hemostasis Ability | Forearm Adhesion (days) |
|---|---|---|---|---|
| 34 | 5 | 1 | yes, fluid | |
| 35 | 10 | 1 | yes | |
| 36 | 15 | 1 | yes | |
| 37 | 20 | 1 | yes, crusty | |
| 38 | 30 | 1 | yes, crusty | 3 |

With this series of tests, Examples 35-38 provided good results with forearm adhesion of 3 days (Example 38), low tack and instant blood coagulation. Example 34 is also useful as liquid adhesive bandage with gentle hemostasis requirements.

Examples 39-43

Testing of cyanoacrylate/polsiloxysilane solution (SOL3)

n-Butyl cyanoacrylate (BCA) was mixed with a solution containing poly(3-methacryloyloxypropyltris(trimethylsiloxy)silane-co-n-butyl methacrylate (PSS3) and hexamethyldisiloxane. This polysiloxysilane solution shall be abbreviated as SOL3 (solution three) in the following references. The formulations were tested as in Examples 34-38.

| Ex | BCA to SOL3 (wt % of soln.) | Tack | Hemostasis Ability | Forearm Adhesion (days) |
|---|---|---|---|---|
| 39 | 5 | 1 | yes, | |
| 40 | 10 | 1 | yes | |
| 41 | 15 | 1 | yes | |
| 42 | 20 | 1 | yes | |
| 43 | 30 | 1 | yes, crusty | 2 |

With this series of tests, Examples 39-43 provided reasonable results with forearm adhesion of 2 days (Example 43), low tack and instant blood coagulation.

Examples 44-47

Butyl Cyanoacrylate Tested with Hydrocarbon Liquid n-Butyl cyanoacrylate (BCA) was mixed into 2,2,4-trimethylpentane (TMP), a volatile, non-reactive hydrocarbon, to form liquid adhesive compositions. These liquid adhesive compositions were then tested. Hemostasis ability was tested by pipetting 5 µl of pork blood on a microscope slide immediately followed by pipetting 5 µl of the liquid adhesive composition directly on top of the blood droplet.

In addition to hemostasis testing, adhesion of two surfaces that are pressed together in the presence of the compositions was tested. 5 µl of the compositions was pipetted onto a glass slide, allowed to dry/react for about 10 seconds, and then another glass slide was pressed onto the coated first slide. After about 1 minute, force was applied to the glass slides to pull them apart.

The data suggest that at cyanoacrylate concentrations above 50% (Examples 46 and 47), the positive benefits of incorporated volatile, non-reactive liquid are diminished.

Below 50% BCA concentration in TMP (Examples 44 and 45), two glass surfaces do not adhere to each other when the liquid adhesive composition is applied, although the desired result of hemostasis does occur.

| Ex | BCA/TMP (wt %) | Hemostasis Ability | Adhesion to two glass surfaces |
|---|---|---|---|
| 44 | 13.5 | coagulation | no |
| 45 | 30 | coagulation | no |
| 46 | 50 | explosive coagulation | yes |
| 47 | 80 | explosive coagulation | yes |

Examples 48-50

Testing of Butyl cyanoacrylate/polysiloxysilane in 2,2,4-trimethylpentane

Butyl cyanoacrylate (BCA) was mixed at various concentrations with a solution containing poly(3-methacryloyloxypropyltris(trimethylsiloxy)silane-co-methyl methacrylate-co-isooctyl acrylate) (PSS1) and 2,2,4-trimethylpentane (TMP). The polymer was dissolved at 10 wt % solids into the 2,2,4-trimethylpentane solvent. Hemostasis ability and adhesion to two surfaces testing was conducted as in Examples 17-20 and Examples 26-28.

| Ex | BCA (% of solution by wt) | Hemostasis Ability | Adhesion of two surfaces Glass |
|---|---|---|---|
| 48 | 8% BCA/PSS1/TMP (40% BCA by % solids) | coagulation | no |
| 49 | 27% BCA/PSS1/TMP | coagulation | moderate |
| 50 | 35% BCA/PSS1/TMP | explosive coagulation | yes |

With this volatile solvent, less than 35% BCA in the polysiloxysilane solution is necessary to provide non-explosive coagulation (Examples 48 and 49). Below 27% is needed to also have non-adhesion of two surfaces (Example 48).

Other Embodiments

The above examples are representative of specific embodiments of the present invention. However, many variations are possible. In all forms, the liquid hemostatic coating material of this invention comprises a reactive cyanoacrylate monomer and a solvent system comprising a volatile, non-reactive liquid and which can further comprise a polymer component containing siloxysilane functional groups. In all cases the invention provides a method of forming a hemostatic coating on a surface by applying a liquid monomeric cyanoacrylate or a liquid monomeric cyanoacrylate with or without a polysiloxysilane, in an inert volatile solvent, to a surface, which may be bloody; and volatilizing the solvent system, while concurrently polymerizing the cyanoacrylate and attaching it to the applied surface. In the presence of the polysiloxysilane, an interpenetrating network is presumably formed, generating a strong, cohesive film. For these systems, the cyanoacrylate attaches to the applied surface providing hemostatic function and the evaporation of the volatile solvent from the coating formulation prevents adhesion of the cyanoacrylate to a second surface.

REFERENCES

U.S. application Ser. No. 09/430,289 filed Oct. 29, 1999
U.S. Pat. No. 3,940,362 Overhults
U.S. Pat. No. 4,313,865 Teramoto, et al.
U.S. Pat. No. 4,560,723 Millet, et al.
U.S. Pat. No. 4,987,893, Salamone, et al.
U.S. Pat. No. 5,103,812, Salamone, et al.
U.S. Pat. No. 5,140,084 Mikuni, et al.
U.S. Pat. No. 5,214,093 Nell, et al.
U.S. Pat. No. 5,259,835 Clark, et al.
U.S. Pat. No. 5,328,687 Leung, et al.
U.S. Pat. No. 5,928,611 Leung, et al.
U.S. Pat. No. 5,981,621 Clark, et al.
U.S. Pat. No. 6,010,714 Leung, et al.
U.S. Pat. No. 6,143,352 Clark, et al.
U.S. Pat. No. 6,143,805 Hickey, et al.
U.S. Pat. No. 6,183,593 Narang, et al.
U.S. Pat. No. 6,217,603 Clark, et al.
U.S. Pat. No. 6,358,503 Gerrish
U.S. Pat. No. 6,383,502 Dunshee, et al.
U.S. Pat. No. 6,455,064 Narang, et al.
U.S. Pat. No. 6,479,725 Brothers
U.S. Pat. No. 6,565,840 Clark, et al.
U.S. Pat. No. 6,746,667 Badejo, et al.
S. C. Davis, W. H. Eaglstein, A. L. Cazzaniga, P. M. Mertz, Dermatologic Surgery, 2001, 27, pp 783-788.
W. H. Eaglstein, T. P. Sullivan, P. A. Giordano, B. M. Miskin, Dermatologic Surgery, 2002, 28, pp 263-267.
A. J. Singer, L. Berrutti, S. A. McClain, Wound Repair and Regeneration, 1999, 7, pp. 356-361.
A. J. Singer, M. Nable, P. Cameau, D. D. Singer, S. A. McClain, Wound Repair and Regeneration, 2003, 11, pp. 181-187.
C. Vauthier, C. Dubemet, E. Fattal, H. Pinto-Alphandary, P. Couvreur, Advanced Drug Delivery Reviews, 55, Issue 4, pp 519-548.

What is claimed is:

1. A liquid coating material comprising about 0.5 to about 50 wt % polymerizable cyanoacrylate monomer and about 10 to about 99.9 wt % of a volatile liquid selected from the group consisting of volatile linear and cyclic siloxanes, volatile polydimethylsiloxanes, isooctane, octane, and combinations thereof,
   said volatile liquid being present in an amount such that the liquid coating material does not adhere to a second glass surface, when:
      (i) the liquid coating material is applied to a first glass surface, and
      (ii) the second glass surface is applied to the first glass surface, having the liquid coating material disposed there between,
   said coating material forming an adherent, conformable polymer coating when applied to a surface, wherein said volatile liquid volatilizes at room or body temperature.

2. A liquid coating material in accordance with claim 1, wherein said polymerizable cyanoacrylate monomer component comprises alpha-cyanoacrylates.

3. A liquid coating material according to claim 2, wherein said alpha-cyanoacrylate monomer component comprises at least one of: n-butyl cyanoacrylate and 2-octyl cyanoacrylate.

4. A liquid coating material according to claim 1, wherein the volatile liquid comprises a liquid selected from the group consisting of hexamethyldisiloxane, octamethylcyclotetrasiloxane, decamethylcyclopentasiloxane, octamethyltrisiloxanes and combinations thereof.

5. A liquid coating material according to claim 1, comprising: hexamethyldisiloxane as the volatile liquid.

6. A liquid coating material comprising about 0.5 to about 50 wt % polymerizable cyanoacrylate monomer and about 10 to about 99.9 wt % of a volatile liquid selected from the group consisting of volatile linear and cyclic siloxanes, volatile polydimethylsiloxanes, isooctane, octane, and combinations thereof,
said volatile liquid being present in an amount such that the liquid coating material does not adhere to a second glass surface, when:
(i) the liquid coating material is applied to a first glass surface, and
(ii) the second glass surface is applied to the first glass surface, having the liquid coating material disposed there between,
said coating material forming an adherent, conformable polymer coating when applied to a surface.

7. A liquid coating material comprising about 0.5 to about 50 wt % polymerizable cyanoacrylate monomer and about 10 to about 99.9 wt % of a volatile liquid selected from the group consisting of volatile linear and cyclic siloxanes, volatile polydimethylsiloxanes, isooctane, octane, and combinations thereof,
said volatile liquid being present in an amount such that the liquid coating material does not adhere to a second glass surface, when:
(i) the liquid coating material is applied to a first glass surface, and
(ii) the second glass surface is applied to the first glass surface, having the liquid coating material disposed there between,
said coating material forming an adherent, conformable polymer coating upon polymerization of the aipha-cyanoacrylate monomer and volatilization of the non-reactive solvent when said coating is applied to a surface, wherein said volatile liquid volatilizes at room or body temperature.

8. A liquid coating material in accordance with claim 7, comprising n-butyl cyanoacrylate as the cyanoacrylate monomer and hexamethyldisiloxane as the volatile solvent.

9. A kit comprising: a liquid coating material comprising about 0.5 to about 50 wt % polymerizable cyanoacrylate monomer and about 10 to about 99.9 wt % of a volatile liquid selected from the group consisting of volatile linear and cyclic siloxanes, volatile polydimethylsiloxanes, isooctane, octane, and combinations thereof,
said volatile liquid being present in an amount such that the liquid coating material does not adhere to a second glass surface, when:
(i) the liquid coating material is applied to a first glass surface, and
(ii) the second glass surface is applied to the first glass surface, having the liquid coating material disposed there between,
said coating material forming an adherent, conformable polymer coating when applied to a surface, wherein said volatile liquid volatilizes at room or body temperature.

10. A kit accordance with claim 9, wherein said polymerizable cyanoacrylate monomer component comprises alpha-cyanoacrylates, wherein said aipha-cyanoacrylate monomer component comprises at least one of: n-butyl cyanoacrylate and 2-octyl cyanoacrylate.

11. A kit comprising: a liquid coating material comprising about 0.5 to about 50 wt % polymerizable cyanoacrylate monomer and about 10 to about 99.9 wt % of a volatile liquid selected from the group consisting of volatile linear and cyclic siloxanes, volatile polydimethylsiloxanes, isooctane, octane, and combinations thereof,
said volatile liquid being present in an amount such that the liquid coating material does not adhere to a second glass surface, when:
(i) The liquid coating material is applied to a first glass surface, and
(ii) the second glass surface is applied to the first glass surface, having the liquid coating material disposed there between,
said coating material forming an adherent, conformable polymer coating when applied to a surface.

12. A liquid coating material comprising about 0.5 to about 50 wt % polymerizable cyanoacrylate monomer and about 10 to about 99.9 wt % of a volatile liquid selected from the group consisting of volatile liner and cyclic siloxanes, volatile polydimethylsiloxanes, and combinations thereof,
said volatile liquid being present in an amount such that the liquid coating material does not adhere first and second glass surfaces, when:
(i) the liquid coating material is applied to a first glass surface, and
(ii) a second glass surface is applied to The first glass surface, having the liquid coating material disposed there between,
said coating material forming an adherent, conformable polymer coating when applied to a surface.

13. A kit comprising: a liquid coating material comprising about 0.5 to about 50 wt % polymerizable cyanoacrylate monomer and about 10 to about 99.9 wt % of a volatile liquid selected from the group consisting of volatile linear and cyclic siloxanes, volatile polydimethylsiloxanes, and combinations thereof,
said volatile liquid being present in an amount such that the liquid coating material does not adhere to a second glass surface, when:
(i) the liquid coating material is applied to a first glass surface, and
(ii) the second glass surface is applied to the first glass surface, having the liquid coating material disposed there between,
said coating material forming an adherent, conformable polymer coating when applied to a surface.

14. The liquid coating material of claim 1, wherein the volatile liquid is selected from the group consisting of volatile linear and cyclic siloxanes, volatile polydimethylsiloxanes, and combinations thereof.

15. The liquid coating material of claim 6, wherein the volatile liquid is selected from the group consisting of volatile linear and cyclic siloxanes, volatile polydimethylsiloxanes, and combinations thereof.

16. The liquid coating material of claim 7, wherein the volatile liquid is selected from the group consisting of volatile linear and cyclic siloxanes, volatile polydimethylsiloxanes, and combinations thereof.

17. The kit of claim 9, wherein the volatile liquid is selected from the group consisting of volatile linear and cyclic siloxanes, volatile polydimethylsiloxanes, and combinations thereof.

18. The kit of claim 11, wherein the volatile liquid is selected from the group consisting of volatile linear and cyclic siloxanes, volatile polydimethylsiloxanes, and combinations thereof.

* * * * *